US010724031B2

(12) United States Patent
Park et al.

(10) Patent No.: US 10,724,031 B2
(45) Date of Patent: Jul. 28, 2020

(54) HIGHLY ACTIVE SILICA MAGNETIC NANOPARTICLES FOR PURIFYING BIOMATERIAL AND PREPARATION METHOD THEREOF

(71) Applicant: BIONEER CORPORATION, Daejeon (KR)

(72) Inventors: Han Oh Park, Daejeon (KR); Jae Ha Kim, Daejeon (KR); Jong Gwang Park, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 0 days.

(21) Appl. No.: 16/586,507

(22) Filed: Sep. 27, 2019

(65) Prior Publication Data

US 2020/0024592 A1 Jan. 23, 2020

Related U.S. Application Data

(62) Division of application No. 14/854,783, filed on Sep. 15, 2015, now Pat. No. 10,465,184.

(30) Foreign Application Priority Data

May 28, 2015 (KR) ........................ 10-2015-0074861

(51) Int. Cl.
*H01F 1/06* (2006.01)
*C12N 15/10* (2006.01)
*H01F 1/00* (2006.01)
*C01B 33/18* (2006.01)

(52) U.S. Cl.
CPC .......... *C12N 15/1013* (2013.01); *C01B 33/18* (2013.01); *H01F 1/0054* (2013.01); *H01F 1/06* (2013.01); *C01P 2004/64* (2013.01); *C01P 2006/42* (2013.01)

(58) Field of Classification Search
None
See application file for complete search history.

(56) References Cited

U.S. PATENT DOCUMENTS

| | | | |
|---|---|---|---|
| 5,523,231 A | 6/1996 | Reeve | |
| 5,665,554 A | 9/1997 | Reeve et al. | |
| 5,945,525 A | 8/1999 | Uematsu et al. | |
| 6,027,945 A | 2/2000 | Smith et al. | |
| 6,673,631 B1 | 1/2004 | Tereba et al. | |
| 7,183,002 B2 | 2/2007 | Sauer et al. | |
| 8,697,020 B2 | 4/2014 | Kim et al. | |
| 2004/0067503 A1 | 4/2004 | Tan et al. | |
| 2004/0101822 A1* | 5/2004 | Wiesner ................. | C09K 11/06 435/5 |
| 2004/0265233 A1 | 12/2004 | Holzer et al. | |
| 2008/0095852 A1 | 4/2008 | Kong et al. | |
| 2011/0054162 A1 | 3/2011 | Kim et al. | |
| 2011/0245483 A1* | 10/2011 | Euting ................ | C12N 15/1013 536/25.41 |
| 2011/0293940 A1* | 12/2011 | Tokoro ...................... | B22F 1/02 428/404 |
| 2012/0208026 A1 | 8/2012 | Zhou et al. | |
| 2013/0089614 A1 | 4/2013 | Zhang et al. | |
| 2016/0348094 A1 | 12/2016 | Park et al. | |

FOREIGN PATENT DOCUMENTS

| | | | |
|---|---|---|---|
| CN | 103406078 A | 11/2013 | |
| CN | 103500622 A | 1/2014 | |
| CN | 104655759 A | 5/2015 | |
| DE | 19614136 A1 | 10/1997 | |
| EP | 1468430 B1 * | 10/2004 | ............... C12Q 1/68 |
| EP | 2600359 A1 | 6/2013 | |
| JP | 3253638 B2 | 2/2002 | |
| JP | 2004031792 A | 1/2004 | |
| JP | 2007089563 A | 4/2007 | |
| JP | 2015024407 A | 2/2015 | |
| KR | 10-2006-0061494 A | 6/2006 | |
| KR | 10-0762969 B1 | 10/2007 | |
| KR | 10-2009-0088299 A | 8/2009 | |
| KR | 10-2010-0097576 A | 9/2010 | |
| KR | 101413958 A1 | 6/2014 | |
| KR | 101413958 B1 | 6/2014 | |
| WO | 9831840 | 7/1998 | |
| WO | 9851114 A1 | 11/1998 | |
| WO | 03038842 A1 | 5/2003 | |

OTHER PUBLICATIONS

English translation of EP 1468430 B1 provided by the WIPO IP Portal [retrieved on Oct. 24, 2019]. Retrieved from the Internet: <URL: https://patentscope.wipo.int/search/en/detail.jsf?docId=EP14213617&tab=PCTDESCRIPTION&_cid=P12-K24ZFU-12605-1>).*
Caiquan, Z., "Preparation of Fe3O4 magnetic composite microspheres and application thereof in automatic extraction of genomic DNA from whold blood; Chinese Masters Thesis Full-text Database", "Engineering Technology", 2010, vol. 1, No. 9.
Shi, B., et al., "Superparamagnetic aminopropyl-functionalized silica core-shell microspheres as magnetically separable carriers for immobilization of penicillin G acylase", "Journal of Molecular Catalysis B: Enzymatic", Jan. 4, 2010, pp. 50-56, vol. 63.

* cited by examiner

*Primary Examiner* — Robert T. Crow
(74) *Attorney, Agent, or Firm* — Hultquist, PLLC; Steven J. Hultquist

(57) ABSTRACT

The present invention relates to a method for preparing highly active silica magnetic nanoparticles, highly active silica magnetic nanoparticles prepared by the method, and a method of isolating nucleic acid using the highly active silica magnetic nanoparticles. The highly active silica magnetic nanoparticles prepared according to the present invention contain magnetic nanoparticles completely coated with silica, can be used as a reagent for isolating biomaterials, particularly, nucleic acids, and can isolate and purify nucleic acid in a high yield.

4 Claims, 4 Drawing Sheets

HIGHLY ACTIVE SILICA MAGNETIC NANOPARTICLES FOR PURIFYING BIOMATERIAL AND PREPARATION METHOD THEREOF

CROSS-REFERENCE TO RELATED APPLICATIONS

This is a divisional under 35 USC § 120 of U.S. patent application Ser. No. 14/854,783 filed Sep. 15, 2015, claiming the priority of Korean Patent Application 10-2015-0074861 filed May 28, 2015. The disclosures of U.S. patent application Ser. No. 14/854,783 and Korean Patent Application 10-2015-0074861 are hereby incorporated herein by reference, in their respective entireties, for all purposes.

TECHNICAL FIELD

The present invention relates to a method for preparing highly active silica magnetic nanoparticles, highly active silica magnetic nanoparticles prepared by the method, a composition and kit for nucleic acid isolation and diagnosis comprising the highly active silica magnetic nanoparticles, and nucleic acid isolation and diagnosis methods that use the highly active silica magnetic nanoparticles.

BACKGROUND ART

Many studies on the use of magnetic particles as bio-related materials have recently been attempted. Magnetic particles started to be frequently used as basic materials in bioengineering research, and have been used for the rapid and simple isolation of biomaterials. Conventional methods for the isolation of biomaterials, particularly, nucleic acids, are processes requiring large amounts of time and labor, and comprise several extraction and centrifugation steps, but the yield and purity of nucleic acids isolated by these methods were low, and these methods were not suitable for the automated or high-throughput isolation of biomaterials. However, in recent studies, special magnetic particles were prepared, and methods of rapidly and efficiently isolating nucleic acids using magnetic particles under suitable buffer conditions were developed (U.S. Pat. Nos. 5,523,231 and 5,665,554). In addition, the use of the above methods for nucleic acid isolation can provide an automated method capable of isolating nucleic acids by treating a large number of samples at the same time. For example, the use of an automated robotic system can isolate a large amount of a desired nucleic acid by automatically treating several hundred or thousand samples.

Isolation of nucleic acids (DNA and RNA) from biological samples is the most important step in biochemical research and diagnostic processes. If isolation of genetic materials from samples is not performed, gene detection, gene cloning, gene sequencing, gene amplification, cDNA synthesis or the like, which is the next step, cannot be performed. To isolate DNA or RNA from various cell mixtures, an effective and reproducible isolation method is required. Thus, isolation methods employing magnetic particles have recently been developed. The method of isolating nucleic acids using magnetic particles comprises inducing the binding of magnetic particles to a gene, and then applying an external magnetic field to the sample to isolate the nucleic acid. It is generally known that the particle size of magnetic particles that are used for the isolation and purification of DNA, RNA, protein or the like is preferably in the range from about 100 nm to about 10 μm.

In order to use magnetic particles for the isolation and purification of genes (nucleic acids) or proteins as described above, a functional group capable of binding to a gene or a specific protein should be conjugated to the surface of the magnetic particles. For this purpose, the magnetic particles should be coated with an organic functional group or silica.

Typical examples of the above-described magnetic particle materials that are used for isolation of biomaterials such as nucleic acids include magnetic iron oxide particles. Magnetic iron oxide particles are generally present as magnetite ($Fe_3O_4$), maghemite ($Fe_2O_3$) or hematite ($Fe_2O_3$), and can be used for the isolation and purification of biomaterials, for example, nucleic acids (DNA and RNA), proteins, peptides and polypeptides, as well as lipids.

In conventional methods for preparing magnetic particles for isolating nucleic acids, magnetic particles, which do not aggregate and interact with one another, can be prepared only when magnetic iron or iron oxide particles are prepared from an iron salt compound by a liquid-phase reduction method and are coated with silica, a polymer or a nonmagnetic material such as gold or silver. In recent years, among such magnetic particles, silica-coated magnetic particles have been mainly developed (U.S. Pat. Nos. 6,027,945, 6,673,631, and 7,183,002, and Japanese Patent No. 3253638). However, such silica-coated magnetic particles have shortcomings in that a process for preparing the silica-coated magnetic particle is complex and the yield of isolation of biomaterials such as nucleic acids by the silica-coated magnetic particles is low.

Accordingly, the present inventor have found that, when a method for the chemical preparation of silica magnetic particles comprises using a silane treatment process and adding an acid-base catalyst to an alcohol solvent to induce a silica formation reaction, it can prepare highly active silica magnetic nanoparticles, thereby completing the present invention.

DISCLOSURE OF INVENTION

Technical Problem

It is an object of the present invention to provide a method for preparing highly active silica magnetic nanoparticles that can purify biomaterials, particularly, nucleic acids, with increased efficiency.

Another object of the present invention is to provide highly active silica magnetic nanoparticles prepared by the above method and having increased nucleic acid purification efficiency.

Still another object of the present invention is to provide a method for isolating and purifying nucleic acid, wherein the highly active silica magnetic nanoparticles are used as nucleic acid-binding carriers.

Yet another object of the present invention is to provide a composition for purifying nucleic acid, which contains the highly active silica magnetic nanoparticles.

A further object of the present invention is to provide a composition for diagnosis based on nucleic acid detection, which contains the highly active silica magnetic nanoparticles.

A still further object of the present invention is to provide a kit for purifying nucleic acid, which contains the highly active silica magnetic nanoparticles.

A yet further object of the present invention is to provide a kit for diagnosis based on nucleic acid detection, which contains the highly active silica magnetic nanoparticles.

Another further object of the present invention is to provide a method wherein the highly active silica magnetic nanoparticles are used in a process selected from the group consisting of protein purification, antibody purification, enzyme immunoassay, peptide purification, and endotoxin removal.

Technical Solution

To achieve the above objects, the present invention provides a method for preparing highly active silica magnetic nanoparticles, the method comprising the steps of: (a) ultrasonically dispersing a solution obtained by adding magnetic nanoparticles, an acid-base catalyst and a water-soluble hydrophobic solvent to a mixed solvent of distilled water and alcohol; and (b) adding silane to the dispersed solution to prepare silica magnetic nanoparticles.

The present invention provides highly active silica magnetic nanoparticles having a silica content of 0.5-2.5 wt %, a particle size of 300-600 nm, and a coating thickness of 1-15 nm. Preferably, the highly active silica magnetic nanoparticles according to the present invention may be prepared by the inventive method for preparing highly active silica magnetic nanoparticles.

The present invention also provides a method for isolating and purifying nucleic acid, wherein the highly active silica magnetic nanoparticles are used as nucleic acid-binding carriers.

The present invention also provides a composition for purifying nucleic acid, which contains the highly active silica magnetic nanoparticles.

The present invention also provides a composition for diagnosis based on nucleic acid detection, which contains the highly active silica magnetic nanoparticles.

The present invention also provides a kit for purifying nucleic acid, which contains the highly active silica magnetic nanoparticles.

The present invention also provides a kit for diagnosis based on nucleic acid detection, which contains the highly active silica magnetic nanoparticles.

The present invention also provides a method wherein the highly active silica magnetic nanoparticles are used in a process selected from the group consisting of protein purification, antibody purification, enzyme immunoassay, peptide purification, and endotoxin removal.

Advantageous Effects

As described above, the highly active silica magnetic nanoparticles prepared according to the present invention contain magnetic nanoparticles completely coated with silica, can be used as a reagent for isolating biomaterials, particularly, nucleic acids, and can isolate and purify nucleic acid in a high yield. In addition, the highly active silica magnetic nanoparticles can also be used for protein purification, antibody purification, enzyme immunoassay, peptide purification, endotoxin removal and the like.

BEST MODE FOR CARRYING OUT THE INVENTION

Figure 1:
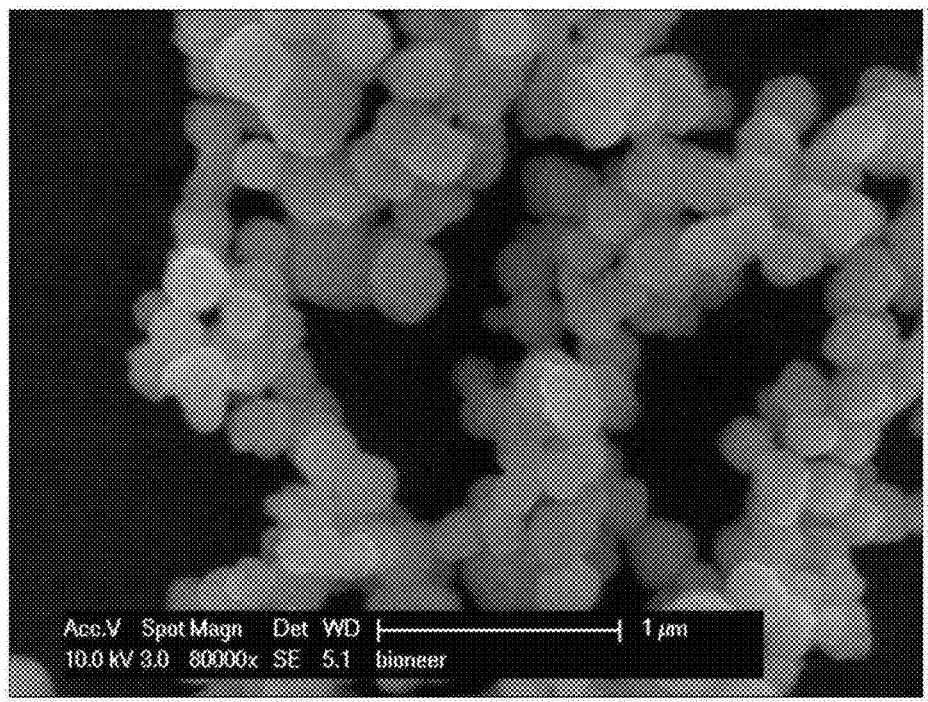
FIG. 1 is a scanning electron microscope (SEM) photograph of highly active silica magnetic nanoparticles prepared in Example 1.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

The present inventors have developed a novel method for preparing silica magnetic nanoparticles, which is simpler than a conventional method for preparing silica magnetic particles and can control the amount of silica coated on silica magnetic particles. According to the present invention, highly active silica magnetic nanoparticles having a high extraction efficiency for nucleic acid compared to conventional silica magnetic particles can be prepared by using nano-sized silica magnetic particles that provide a maximized surface area.

Thus, in one aspect, the present invention is directed to a method for preparing highly active silica magnetic nanoparticles, the method comprising the steps of: (a) ultrasonically dispersing a solution obtained by adding magnetic nanoparticles, an acid-base catalyst and a water-soluble hydrophobic solvent to a mixed solvent of distilled water and alcohol; and (b) adding silane to the dispersed solution to prepare silica magnetic nanoparticles.

The solvent that is used in the preparation method according to the present invention is a mixed solvent of distilled water and alcohol. The alcohol that is used in the present invention is preferably methyl alcohol, ethyl alcohol, propyl alcohol, butyl alcohol, or a mixture of two or more thereof, but is not limited thereto. In addition, the distilled water that is used in the present invention is preferably double-distilled water or triple-distilled water (ultrapure water).

In the present invention, the mixed solvent preferably contains 30 vol % or less of distilled water.

In the preparation method according to the present invention, a silane compound is added in step (b) of the method. Herein, the silane compound reacts with the acid-base catalyst to form a silica coating on the surface of the magnetic nanoparticles.

Examples of silane that can be used in the preparation method according to the present invention include, but are not limited to, tetramethoxysilane, tetraethoxysilane or a mixture thereof.

The silane compound may be added in an amount of 0.01-0.5 parts by volume, preferably 0.01-0.2 parts by volume based on 100 parts by volume of the total volume of distilled water and alcohol that are used as a solvent, and the acid-based catalyst and water-soluble hydrophobic solvent added. If the silane compound is added in an amount of more than 0.5 parts by volume, it will influence silica formation, and thus silica magnetic nanoparticles will aggregate, and if the silane compound is added in an amount of less than 0.01 parts by volume, a silica coating will not be formed on the surface of the magnetic nanoparticles.

Examples of the acid-base catalyst that is used in the present invention include, but are not limited to, ammonia water ($NH_4OH$), ammonium fluoride ($NH_4F$), hydrochloric acid (HCl), nitric acid ($HNO_3$), sulfuric acid ($H_2SO_4$), phosphoric acid ($H_3PO_4$), fluoric acid (HF), oxalic acid, and acetic acid. Preferably, ammonia water may be used.

In addition, the preparation method according to the present invention is characterized in that the thickness of silica coated on the surface of the silica magnetic nanoparticles can be controlled according to the amount of silane compound added.

The magnetic nanoparticles that are used in the preparation method according to the present invention are metal nanoparticles made of one or more selected from the group consisting of iron oxide (hematite, maghemite ($Fe_2O_3$) or magnetite ($Fe_3O_4$)), ferrite, iron, cobalt, nickel, iron oxides, cobalt oxides, nickel oxides, and mixtures thereof, but are not limited thereto. Most preferably, the magnetic nanoparticles are iron oxide (magnetite) nanoparticles having a particle size of 100-500 nm. Iron oxide magnetic nanoparticles that are used in the present invention may be prepared by synthesis or commercially purchased. Specifically, iron oxide, ferrite or a mixture thereof may be used.

In one method, iron oxide magnetic nanoparticles can, for example, be prepared by instantaneously injecting carbonyl iron into a high-temperature solvent to prepare iron magnetic particles while generating carbon dioxide by pyrolysis, and oxidizing the prepared iron magnetic particles. Another preparation method, a method of preparing iron oxide by adding ammonia water ($NH_4OH$) to a mixture of $FeCl_2$ and $FeCl_3$ is also widely known.

The magnetic nanoparticles may be used in an amount of 0.01-0.5 parts by weight, preferably 0.05-0.3 parts by weight, based on 100 parts by weight of the total weight of distilled water, alcohol, the acid-base catalyst and the water-soluble hydrophobic solvent. If the magnetic nanoparticles are used in an amount of more than 0.5 parts by weight, there will be a problem in that silica magnetic nanoparticles will aggregate, and if the magnetic nanoparticles are used in an amount of less than 0.01 parts by weight, there will be a problem in that the number of magnetic particles contained in the solvent is too small, and thus productivity is low.

The water-soluble hydrophobic solvent that is used in the present invention is preferably selected from the group consisting of pentane, cyclopentane, hexane, cyclohexane, toluene, benzene, xylene, diethyl ether, dioxane, chloroform, and dichloromethane, but is not limited thereto. More preferably, the water-soluble hydrophobic solvent may be toluene.

In the present invention, the magnetic nanoparticles and the silane compound are preferably added at a weight ratio of 1:0.1-1:3.0. If the magnetic nanoparticles and the silane compound are added at a weight ratio of more than 1:3.0, there will be a problem in that silica magnetic nanoparticles aggregate, and if these are added at a weight of less than 1:0.1, there will be a problem in that silica coating is not sufficient.

In addition, the preparation method according to the present invention may further comprise, after step (b), conventional filtering, washing and drying steps. The filtering step is performed using filter paper, and the washing step is performed by washing the filtered material several times with ethanol and ultrapure water. The drying step that is the final step is performed by drying the prepared silica magnetic nanoparticles in an air-circulated dryer for 2 hours or more at a temperature of 100 to 300° C., preferably 100 to 200° C.

In another aspect, the present invention is directed to highly active silica magnetic nanoparticles having a silica content of 0.5-2.5 wt %, a particle size of 300-600 nm, and a coating thickness of 1-15 nm.

In the present invention, the highly active silica magnetic nanoparticles may be prepared by the above-described method for preparing highly active silica magnetic nanoparticles.

Highly active silica magnetic nanoparticles that are prepared according to an embodiment of the present invention have a particle size of 400-450 nm as shown in FIGS. 1, 2, 5 and 6.

Spherical silica magnetic nanoparticles prepared by the preparation method of the present invention are magnetic particles (having a particle size of several ten to several hundred nanometers) coated with silica, and show a negative zeta potential (−30 to −50 mV) due to the hydroxyl group of silica.

In still another aspect, the present invention is directed to a method for isolating and purifying nucleic acid, wherein the highly active silica magnetic nanoparticles are used as nucleic acid-binding carriers.

A method of isolating nucleic acid using silica is performed using a chaotropic reagent, and is a widely known method (R. Boom et al., J. Clin. Microbiol., Vol 28(3), p 495-503 (1990)). In this method, when magnetic particles coated with silica bind to nucleic acid by the chaotropic reagent, and the nucleic acid is isolated by separating the silica magnetic particles using an external magnetic force.

Highly active silica magnetic nanoparticles prepared by the preparation method of the present invention are used to isolate various types of nucleic acids, including, but not limited to, plasmid DNA, genomic DNA, cDNA, PCR DNA (polymerase chain reaction DNA), RNA, siRNA, ribozymes, aptamers, oligonucleotides and DNA primers.

A method of isolating and purifying nucleic acid using the highly active silica magnetic nanoparticles of the present invention is as follows. In the first step, the highly active silica magnetic nanoparticles of the present invention are added to a sample containing the nucleic acid to be isolated to induce the binding of the nucleic acid to the silica magnetic nanoparticles. Herein, a binding buffer is used. As the binding buffer, a chaotropic reagent is used. Chaotropic reagents include guanidine salt, urea, chloride, iodide, perchlorate, (iso)thiocyanate and the like, and specific examples include, but are not limited to, sodium perchlorate, guanidine hydrochloride, guanidine isothiocyanate, potassium iodide, potassium thiocyanate, sodium chloride, sodium isothiocyanate, magnesium chloride, sodium iodide, etc. The chaotropic reagent is preferably used at a concentration of 1-8 M (mol/L).

The second step of the method for nucleic acid isolation is a step of isolating the silica magnetic nanoparticles having the nucleic acid bound thereto. In this step, the silica magnetic nanoparticles having the nucleic acid bound thereto are collected on the wall of the container by an external magnetic force, and unbound material is separated, followed by washing.

The third step is a step of removing the external magnetic force and isolating the nucleic acid from the silica magnetic nanoparticles having the nucleic acid bound thereto. In this step, the nucleic acid bound to the silica magnetic particles is isolated using an elution buffer (tris-(hydroxymethyl) amino methane buffer).

It could be seen that highly active silica magnetic nanoparticles prepared in Example 1 of the present invention isolated nucleic acid in a very high yield. Thus, it can be seen that highly active silica magnetic nanoparticles prepared according to the present invention isolate nucleic acid with high efficiency.

In yet another aspect, the present invention is directed to a composition and kit for purifying nucleic acid, which contains the highly active silica magnetic nanoparticles.

A composition or kit for nucleic acid purification may comprise a chaotropic reagent for binding nucleic acid to the silica magnetic nanoparticles.

The kit for nucleic acid purification according to the present invention may comprise a binding buffer for binding nucleic acid to the silica magnetic nanoparticles, a washing buffer, an elution buffer, and a magnet for isolating the silica magnetic nanoparticles.

In a further aspect, the present invention is directed to a composition and kit for diagnosis based on nucleic acid detection, which contains the highly active silica magnetic nanoparticles.

A composition or kit for diagnosis based on nucleic acid detection may comprise a chaotropic reagent for binding nucleic acid to the silica magnetic nanoparticles.

The kit for diagnosis based on nucleic acid detection according to the present invention may comprise a binding buffer for binding nucleic acid to the silica magnetic nanoparticles, a washing buffer, an elution buffer, and a magnet for isolating the silica magnetic nanoparticles.

The kit of the present invention may include an instruction manual. The "instruction manual" is a printed matter describing how to use the kit, for instance, the method of preparing reagents for making nucleic acids, recommended preparation conditions, and the like. The instruction manual includes those appearing on labels attached to the kit, packages housing the kit, and the like, as well as handling brochures in a pamphlet or leaflet form. In addition, the instruction manual includes information that is disclosed or provided via an electronic medium such as the internet.

In a still further aspect, the present invention is directed to a method wherein the highly active silica magnetic nanoparticles are used in a process selected from the group consisting of protein purification, antibody purification, enzyme immunoassay, peptide purification, and endotoxin removal.

For the binding between the highly active silica magnetic nanoparticles and a protein, an enzyme, a peptide or an endotoxin, highly active silica nanoparticles having an amino substituent, prepared by dispersing silica magnetic nanoparticles and then reacting the silica magnetic nanoparticles with an amine-based compound such as 3-aminopropyltriethoxysilane, N-[3-(trimethoxysilyl)propyl]ethylenediamine, or N'-[3-(trimethoxysilyl)propyl]diethylene triamine, can be used.

EXAMPLES

Hereinafter, the present invention will be described in further detail with reference to examples. It will be obvious to a person having ordinary skill in the art that these examples are illustrative purposes only and are not to be construed to limit or change the scope of the present invention.

Example 1: Preparation of Highly Active Silica Magnetic Nanoparticles 1,600 ml of ethanol was placed in a 3-L flask, and 400 ml of ultrapure water was added thereto. Then, 1.5 g of iron oxide magnetic nanoparticles (magnetite; Dreamtech, Korea) were added to the solution and dispersed ultrasonically for 1 hour. To the dispersed solution, 15 ml of ammonia solution (28-30 wt %, Samchun Chemical Co., Ltd.) and 100 ml of toluene (99.5%, Samchun Chemical Co., Ltd.) were added, followed by ultrasonic dispersion for 30 minutes. While the flask was maintained at room temperature, 0.5 ml of tetraethoxysilane (TEOS, 98%, Samchun Chemical Co., Ltd.) was added thereto over 5 minutes, and the mixture was allowed to react at room temperature for 4 hours. After completion of the reaction, the content of the reactor was separated using a filter and washed twice or more with ethanol and ultrapure water. The obtained silica magnetic nanoparticles were dried in a dryer at 120° C. for 2 hours, thereby preparing highly active silica magnetic nanoparticles.

Figure 2:
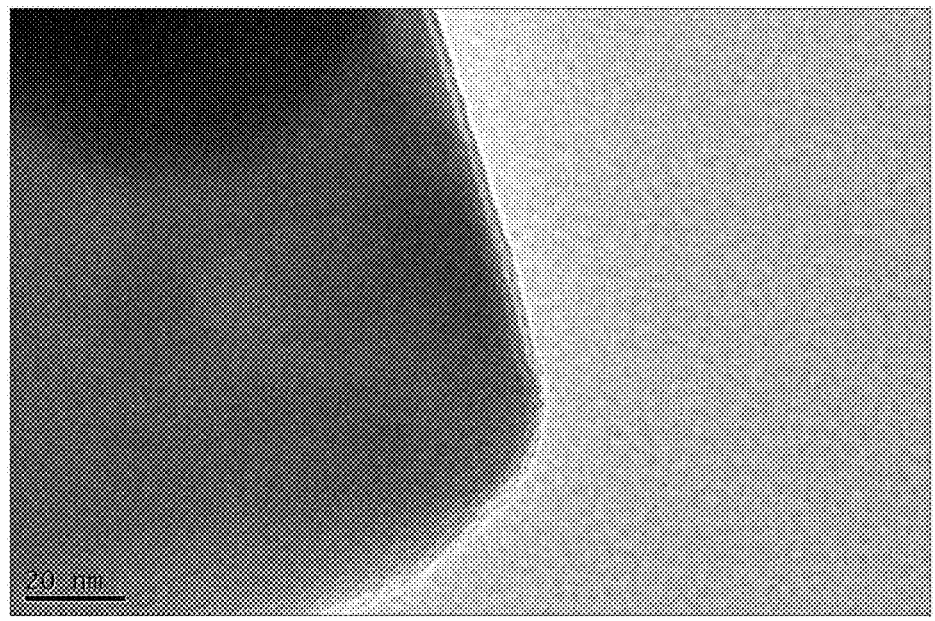
FIG. 2 is a transmission electron microscope (TEM) photograph of highly active silica magnetic nanoparticles prepared in Example 1.

The results of scanning electron microscope (SEM) analysis and transmission electron microscope (TEM) analysis of the prepared highly active silica magnetic nanoparticles are shown in FIGS. 1 and 2, respectively.

As can be seen in FIG. 2, the iron oxide magnetic nanoparticles were coated with silica to a thickness of about 2 nm.

Figure 3:
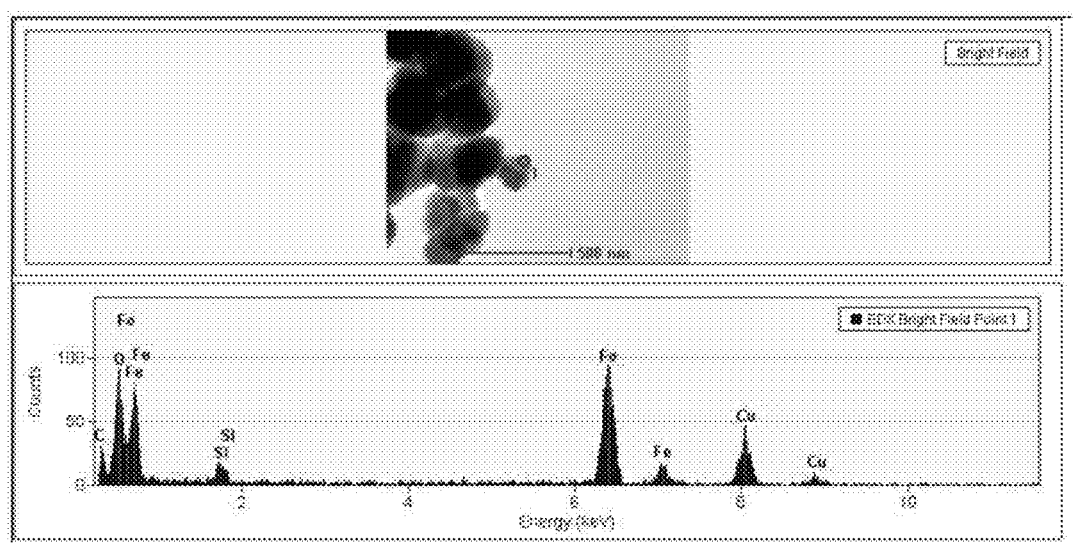
FIG. 3 shows the results of electron microscopy-energy dispersive X-ray spectrometry (TEM-EDS) analysis of highly active silica magnetic nanoparticles prepared in Example 1.
Figure 4:
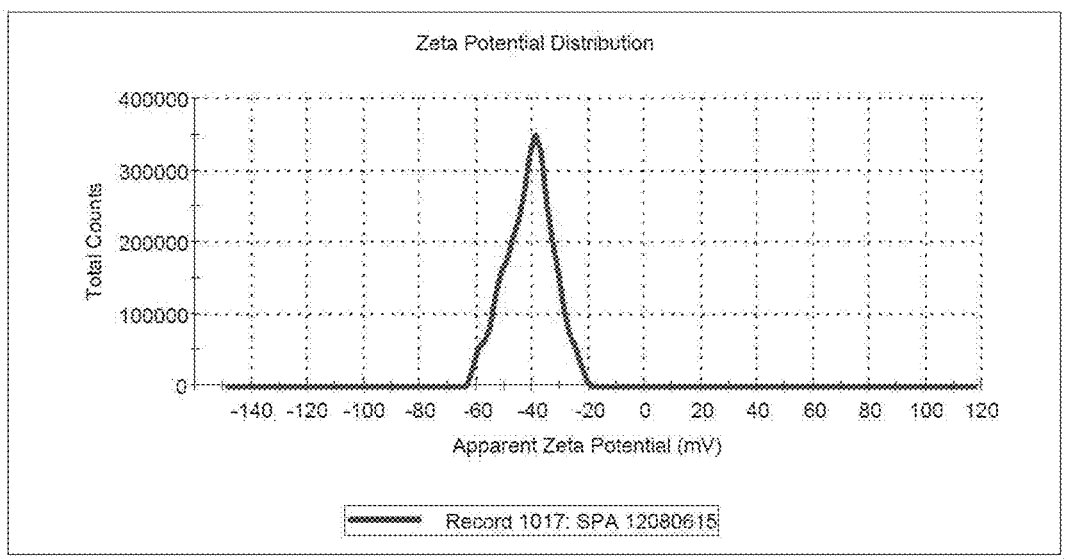
FIG. 4 shows the results of analyzing the zeta potential of highly active silica magnetic nanoparticles prepared in Example 1.

The prepared highly active silica magnetic nanoparticles were analyzed by energy dispersive spectrometry (EDS), and as a result, it was shown that a silica component was detected (FIG. 3). The zeta potential of the prepared highly active silica magnetic nanoparticles was measured to be −41.0 mV, indicating that there was a hydroxyl group on the silica surface (FIG. 4). In addition, the mean particle size of the prepared highly active silica magnetic nanoparticles was measured to be 420 nm.

Example 2: Preparation of Silica Magnetic Nanoparticles by Addition of 2-Fold Amount of TEOS Highly active silica magnetic nanoparticles were prepared in the same manner as described in Example 1, except that the amount of tetraethoxysilane (TEOS, 98%, Samchun Chemical Co., Ltd.) added was increased to 1.0 ml.

Figure 5:
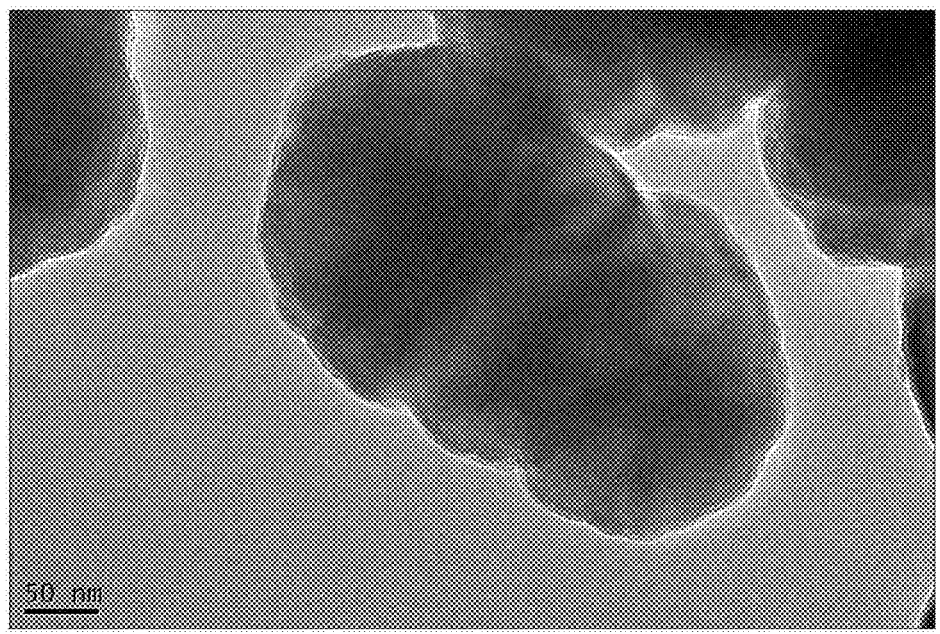
FIG. 5 is a transmission electron microscope (TEM) photograph of highly active silica magnetic nanoparticles prepared in Example 2.

FIG. 5 shows a transmission electron microscope (TEM) photograph of the prepared highly active silica magnetic nanoparticles. As shown therein, the iron oxide magnetic nanoparticles were coated with silica to a thickness of about 5 nm, which was thicker than that in Example 1. The zeta potential of the prepared highly active silica magnetic nanoparticles was measured to be −33.2 mV, indicating that there was a hydroxyl group on the silica surface. In addition, the mean particle size of the prepared highly active silica magnetic nanoparticles was measured to be 430 nm.

Example 3: Preparation of Silica Magnetic Nanoparticles by Addition of 4-Fold Amount of TEOS Highly active silica magnetic nanoparticles were prepared in the same manner as described in Example 1, except that the amount of tetraethoxysilane (TEOS, 98%, Samchun Chemical Co., Ltd.) added was 2.0 ml.

Figure 6:
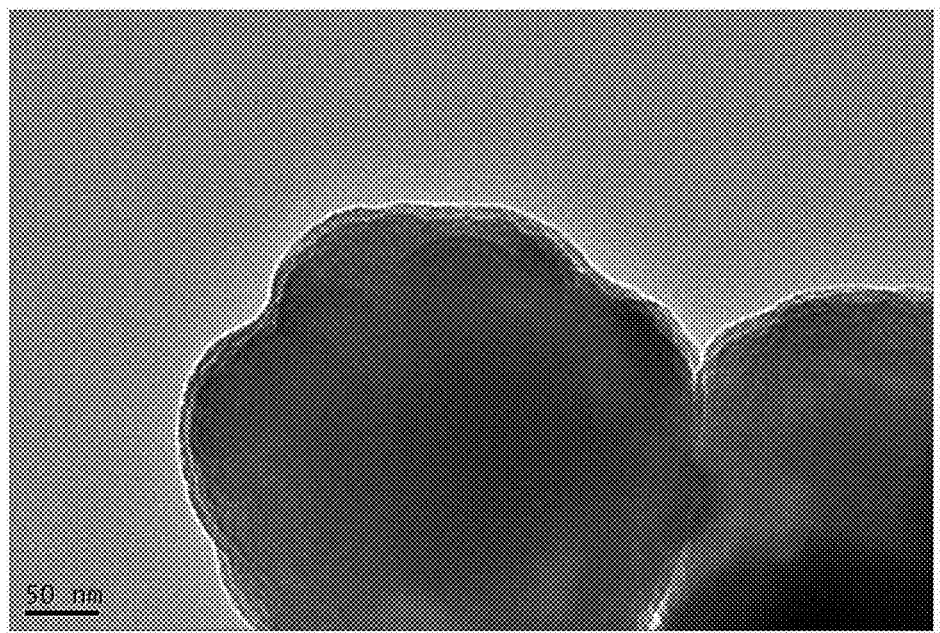
FIG. 6 is a transmission electron microscope (TEM) photograph of highly active silica magnetic nanoparticles prepared in Example 3.

FIG. 6 shows a transmission electron microscope (TEM) photograph of the prepared highly active silica magnetic nanoparticles. As shown in FIG. 6, the iron oxide magnetic nanoparticles were coated with silica to a thickness of about 13 nm, which was thicker than that in Example 1. The zeta potential of the prepared highly active silica magnetic nanoparticles was measured to be −37.1 mV, indicating that there was a hydroxyl group on the silica surface. In addition, the mean particle size of the prepared highly active silica magnetic nanoparticles was measured to be 450 nm.

Table 1 below shows the change in the silica coating thickness of the surface of the magnetic nanoparticles as a function of the amount of TEOS added.

TABLE 1

Coating thicknesses of silica magnetic nanoparticles under various reaction conditions

| LOT | Ethanol (ml) | Ultra-pure water (ml) | Magnetic nanoparticles (g) | TEOS (ml) | Zeta potential (mV) | Coating thickness (nm) |
|---|---|---|---|---|---|---|
| Example 1 | 1,600 | 400 | 1.5 | 0.5 | −41.0 | 2 |
| Example 2 | 1,600 | 400 | 1.5 | 1.0 | −33.2 | 5 |
| Example 3 | 1,600 | 400 | 1.5 | 2.0 | −37.1 | 13 |

Example 4: Isolation of Nucleic Acid Using Highly Active Silica Magnetic Nanoparticles In order to analyze the nucleic acid isolation efficiency of the highly active silica magnetic particles prepared in Example 1, the following experiment was performed.

1 mg of the silica magnetic particles prepared in Example 1 were added to and mixed with a solution containing 200 µl of a DNA sample (a total of 4 ug containing 1 ug of each of 10.2 kb, 5 kb, 2 kb and 1.6 kb fragmented DNAs) and 900 µl of binding solution (BIONEER EXIPREP™ KIT K-3215 binding solution). The silica magnetic particles were isolated from the supernatant using a neodymium magnet, and the supernatant was completely removed therefrom using a micropipette. Specifically, 900 µl of $1^{st}$ washing solution (BIONEER EXIPREP™ KIT K-3215 $1^{st}$ washing solution) was added to the silica magnetic particles and sufficiently mixed using a micropipette, and then the silica magnetic particles were isolated from the supernatant using a neodymium magnet. After the supernatant was completely removed using a micropipette, 1000 µl of $2^{nd}$ washing solution (BIONEER EXIPREP™ KIT K-3215 $2^{nd}$ washing solution) was added to the silica magnetic particles and completely mixed using a micropipette, and then the silica magnetic particles were isolated from the supernatant using a neodymium magnet. After the supernatant was completely removed using a micropipette, 1000 µl of $3^{rd}$ washing solution (BIONEER EXIPREP™ KIT K-3215 $3^{rd}$ washing solution) was added to the silica magnetic particles and completely mixed using a micropipette, and then the silica magnetic particles were isolated from the supernatant using a neodymium magnet. After the supernatant was completely removed using a micropipette, the silica magnetic particles were dried in an oven at 60° C. for 10 minutes to remove the remaining washing solution. 100 µl of elution buffer (BIONEER EXIPREP™ KIT K-3215 elution buffer) was added to the completely dried silica magnetic particles and sufficiently mixed, and the mixture was allowed to stand in a heating block at 60° C. for 5 minutes so that nucleic acid could be easily eluted from the silica magnetic particles. The silica magnetic particles were isolated using a neodymium magnet, and the supernatant containing nucleic acid was collected by a micropipette and transferred into a fresh 1.5 ml tube. For comparison, a DNA extraction experiment was performed in the same manner as described above using 5 mg of conventional silica magnetic particles (ACCUBEAD™ TS-1010 silica magnetic particles).

Figure 7:
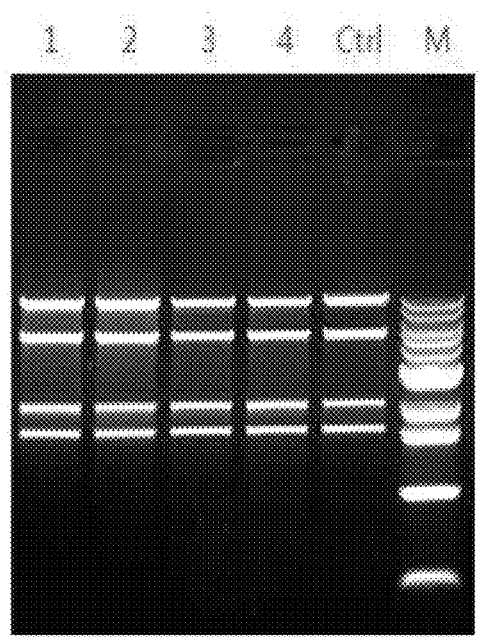
FIG. 7 is an electrophoresis photograph of a DNA extracted using highly active silica magnetic nanoparticles prepared in Example 4.

FIG. 7 is a photograph showing the results of electrophoresis of the DNAs extracted by the above-described method using the conventional micro-sized silica magnetic particles (ACCUBEAD™ TS-1010 silica magnetic particles) and the highly active silica magnetic nanoparticles of the present invention. In FIG. 7, lanes 1 and 2 show the results of electrophoresis of the DNA extracted using the conventional micro-sized silica magnetic particles, and lanes 3 and 4 show the results of electrophoresis of the DNA extracted using the highly active silica magnetic nanoparticles of the present invention, and control (Ctrl) shows the results of electrophoresis of the DNA itself before extraction. From the results of electrophoresis, it can be seen that four different DNAs having different sizes could be easily extracted. In addition, the extracted DNAs were quantitatively analyzed using a UV spectrophotometer, and the results of the analysis are shown in Table 2 below.

TABLE 2

| No. | Amount of DNA input | Amount of beads used | Amount of DNA extracted | Binding Capacity (ug-DNA/mg-beads) |
|---|---|---|---|---|
| 1 | 4 ug | Conventional Micro Beads 5 mg | 3.94 ug | 0.788 |
| 2 | 4 ug | Conventional Micro Beads 5 mg | 3.99 ug | 0.798 |
| 3 | 4 ug | Inventive Nano Beads 1 mg | 2.12 ug | 2.12 |
| 4 | 4 ug | Inventive Nano Beads 1 mg | 2.23 ug | 2.23 |

The results in Table 2 below indicated that the binding capacity of the conventional micro-sized silica magnetic particles was 0.793 ug-DNA/mg-beads, and the binding capacity of the highly active silica magnetic nanoparticles of the present invention was 2.18 ug-DNA/mg-beads. From these results, it can be seen that the binding capacity of the highly active silica magnetic nanoparticles of the present invention is about 2.7 times higher than that of the conventional particles. Therefore, it can be seen that the highly active silica magnetic nanoparticles of the present invention isolate nucleic acid with high efficiency.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:
1. Silica-coated magnetic nanoparticles consisting of magnetic nanoparticles completely coated with silica, wherein a silica content is 0.5-2.5 wt %, a particle size is

420-450 nm, and a coating thickness is 2-13 nm, and surface of the silica has a hydroxyl group thereon.

2. The silica-coated magnetic nanoparticles of claim 1, which are prepared by the method comprising:
   (a) ultrasonically dispersing a solution obtained by adding magnetic nanoparticles, an acid-base catalyst and a hydrophobic organic solvent to a solvent mixture of distilled water and an alcohol; and
   (b) adding silane to the dispersed solution to prepare silica magnetic nanoparticles.

3. A composition for purifying or detecting nucleic acid, which comprises the silica-coated magnetic nanoparticles of claim 1.

4. A kit for purifying or detecting nucleic acid, which comprises the silica-coated magnetic nanoparticles of claim 1.

* * * * *